United States Patent [19]
Hudkins et al.

[11] Patent Number: 6,093,713
[45] Date of Patent: Jul. 25, 2000

[54] 3'-EPIMERIC K-252A DERIVATIVES

[75] Inventors: Robert L. Hudkins, Chester Springs; Diane E. Gingrich, Exton, both of Pa.

[73] Assignees: Kyowa, Hakko, Kogyo Co., Ltd.; Cephalon, Inc., West Chester, Pa.

[21] Appl. No.: 09/223,518

[22] Filed: Dec. 30, 1998

Related U.S. Application Data

[60] Provisional application No. 60/079,263, Dec. 31, 1997.

[51] Int. Cl.$^7$ .......................... A61K 31/55; C07D 498/22
[52] U.S. Cl. .......................... 514/211; 514/213; 540/543; 540/546
[58] Field of Search .................................... 540/545, 546; 514/211, 213

[56] References Cited

U.S. PATENT DOCUMENTS

| | | | |
|---|---|---|---|
| 5,461,146 | 10/1995 | Lewis et al. | 514/211 |
| 5,468,872 | 11/1995 | Glicksman et al. | 548/416 |
| 5,516,772 | 5/1996 | Glicksman et al. | 514/211 |
| 5,585,488 | 12/1996 | Kinugawa et al. | 540/545 |
| 5,621,100 | 4/1997 | Lewis et al. | 540/545 |

FOREIGN PATENT DOCUMENTS

| | | |
|---|---|---|
| 0 303 697 A1 | 2/1989 | European Pat. Off. . |
| 62-155284 | 7/1987 | Japan . |

OTHER PUBLICATIONS

Kaneko et al., J. Med. Chem. 1997, 40, pp. 1863–1869.
Kinugawa, M. et al., "Synthetic Process Development of Antitumor Agent KT6587, an Indolocarbazole Alkaloid K252a Derivative, " Org. Proc. Res. Devel., 1999, 3, 131–134.

Nakanishi, S. et al., "K–252b, c and d, potent inhibitors of protein Kinase C from microbial origin," J. Antibiotics, 1986, vol. XXXIX(8), 1066–1071.
Sezaki, M. et al., "A new antibiotic SF–2370 produced by actinomadura," J. Abtibiotics, 1985, vol. XXXVIII(10), 1437–1439.

*Primary Examiner*—Mukund J. Shah
*Assistant Examiner*—Pavanaram K Sripada
*Attorney, Agent, or Firm*—Woodcock Washburn Kurtz Mackiewicz & Norris LLP

[57] ABSTRACT

Compounds defined by the following general structure are disclosed:

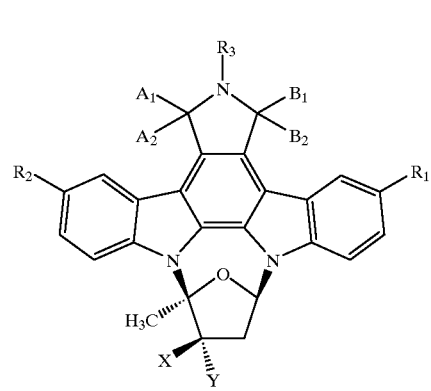

These compounds display pharmacological activities, including inhibition of tyrosine kinase activity and enhancement of the function and/or survival of trophic factor responsive cells, e.g., cholinergic neurons.

12 Claims, 8 Drawing Sheets

IXa (Ex. 10 step 2)

XIX  W = C, O, S, N,
or RW = H (Ex. 10)

3'-EPIMERIC K-252A DERIVATIVES

This application claims benefit of provisional application Ser. No. 60/070,263, filed Dec. 31, 1997.

FIELD OF THE INVENTION

The field of the invention is pharmaceutical chemistry.

BACKGROUND OF THE INVENTION

K-252a is an indolocarbazole whose stereochemistry is shown below (Formula I):

I

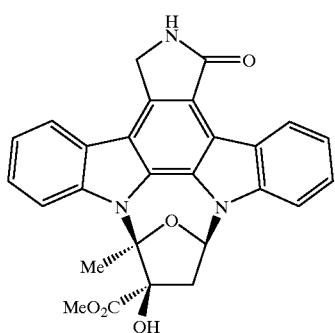

K-252a inhibits protein kinase C (PKC), which plays a role in regulating cell functions. K-252a has various activities, e.g., inhibiting smooth muscle contraction (*Jap. J. Pharmacol.* 43 (suppl.): 284, 1987), inhibiting serotonin secretion (*Biochem. Biophys. Res. Commun.* 144: 35, 1987), inhibiting elongation of neuraxone (*J. Neurosci.* 8:715, 1988), inhibiting histamine release (*Allergy* 43:100, 1988), inhibiting smooth muscle MLCK (*J. Biol. Chem.* 263:6215, 1988), anti-inflammatory action (*Acta Physiol. Hung.* 80:423, 1992), and promotion of cell survival (*J. Neurochem.* 64:1502, 1995). K-252a also inhibits IL-2 production (*Exper. Cell Res.* 193:175–182, 1991). The total synthesis of the natural (+) isomer of K252a and its enantiomeric (−) isomer (all three chiral carbons of the sugar moiety inverted), has been achieved (Wood et al., *J. Am. Chem. Soc.* 117:10413, 1995; and WO 97/07081).

SUMMARY OF THE INVENTION

We have discovered that certain 3'-epimeric derivatives of K-252a are biologically active. These compounds have the following general formula (Formula II):

II

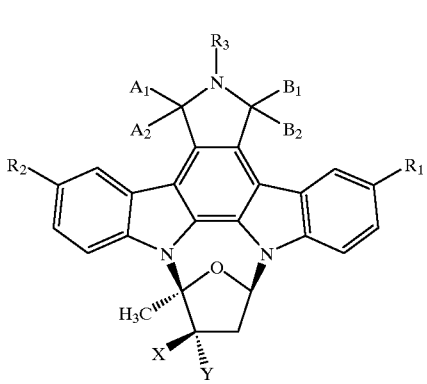

wherein:

$R^1$ and $R^2$ independently are:
hydrogen; lower alkyl; halogen; acyl; nitro; sulfonic acid;

—CH=$NR^4$, wherein $R^4$ is guanidino, heterocyclic, or —$NR^5R^6$, wherein $R^5$ or $R^6$ is hydrogen or lower alkyl, and the other is hydrogen, lower alkyl, acyl, aryl, heterocyclic, carbamoyl or lower alkylaminocarbonyl;

—$NR^5R^6$;

—CH($SR^7$)$_2$, wherein $R^7$ is lower alkyl or alkylene;

—(CH$_2$)$_j R^8$, wherein j is 1–6, and $R^8$ is halogen; substituted aryl; unsubstituted aryl; substituted heteroaryl; unsubstituted heteroaryl; $N_3$;

—CO$_2 R^9$, wherein $R^9$ is hydrogen, substituted lower alkyl, unsubstituted lower alkyl, substituted aryl, unsubstituted aryl, substituted heteroaryl, or unsubstituted heteroaryl;

—C(=O)$NR^{10}R^{11}$, wherein $R^{10}$ and $R^{11}$ independently are hydrogen, substituted lower alkyl, unsubstituted lower alkyl, substituted aryl, unsubstituted aryl, substituted heteroaryl, unsubstituted heteroaryl, substituted aralkyl, unsubstituted aralkyl, lower alkylaminocarbonyl, or lower alkoxycarbonyl, or $R^{10}$ and $R^{11}$ are combined with a nitrogen atom to form a heterocyclic group;

—$OR^{12}$, wherein $R^{12}$ is hydrogen, substituted lower alkyl, unsubstituted lower alkyl, substituted aryl, unsubstituted aryl; or —C(=O)$R^{13}$, wherein $R^{13}$ is hydrogen, $NR^{10}R^{11}$, substituted lower alkyl, unsubstituted lower alkyl, substituted aryl, unsubstituted aryl, substituted heteroaryl, unsubstituted heteroaryl, substituted aralkyl, or unsubstituted aralkyl;

—$NR^{10}R^{11}$;

—C(=O)$R^{14}$, wherein $R^{14}$ is hydrogen, lower alkyl, substituted aryl, unsubstituted aryl, substituted heteroaryl, or unsubstituted heteroaryl;

—S(=O)$_r R^{15}$, wherein r is 0 to 2, and $R^{15}$ is hydrogen, substituted lower alkyl, unsubstituted lower alkyl, substituted aryl, unsubstituted aryl, substituted heteroaryl, unsubstituted heteroaryl, substituted aralkyl, unsubstituted aralkyl, thiazolinyl, (CH$_2$)$_a$CO$_2R^{16}$, wherein a is 1 or 2, and $R^{16}$ is hydrogen or lower alkyl, or —(CH$_2$)$_a$C(=O)$NR^{10}R^{11}$;

—$OR^{17}$, wherein $R^{17}$ is hydrogen, lower alkyl, or —C(=O)$R^{18}$, wherein $R^{18}$ is substituted lower alkyl, unsubstituted lower alkyl, substituted aryl, or unsubstituted aryl;

—C(=O)(CH$_2$)$_j R^{19}$, wherein $R^{19}$ is hydrogen, halogen, $NR^{10}R^{11}$, $N_3$, $SR^{15}$, or $OR^{20}$, wherein $R^{20}$ is hydrogen, substituted lower alkyl, unsubstituted lower alkyl, or C(=O)$R^{14}$;

—CH(OH)(CH$_2$)$_j R^{19}$;

—(CH$_2$)$_d$CHR$^{21}$CO$_2R^{16A}$, wherein d is 0–5, and $R^{21}$ is hydrogen, CONR$^{10}R^{11}$, or CO$_2R^{16A}$, wherein $R^{16A}$ is the same as $R^{16}$;

—(CH$_2$)$_d$CHR$^{21}$CONR$^{10}R^{11}$;

—CH=CH(CH$_2$)$_m R^{22}$, wherein m is 0–4, and $R^{22}$ is hydrogen, lower alkyl, CO$_2R^9$, substituted aryl, unsubstituted aryl, substituted heteroaryl, unsubstituted heteroaryl, $OR^{12}$, or $NR^{10}R^{11}$;

—CH=C(CO$_2R^{16A}$)$_2$;

—C≡C(CH$_2$)$_m R^{22}$;

—SO$_2NR^{23}R^{24}$, wherein $R^{23}$ and $R^{24}$ independently are hydrogen, lower alkyl, or groups that form a heterocycle with the adjacent nitrogen atoms;

—OCO$_2R^{13A}$, wherein $R^{13A}$ is the same as $R^{13}$; or

—OC(=O)$NR^{10}R^{11}$;

$R^3$ is hydrogen; lower alkyl; carbamoyl; amino;

tetrahydropyranyl; hydroxyl; C(=O) H; aralkyl; lower alkanoyl; or $CH_2CH_2R^{25}$, wherein $R^{25}$ is halogen, amino, di-lower alkylamino, hydroxyl, or hydroxysubstituted lower alkylamino;

X is hydrogen; formyl; carboxyl; lower alkoxycarbonyl; lower alkylhydrazinocarbonyl; —CN; lower alkyl;
—C(=O)$NR^{26}R^{27}$, wherein $R^{26}$ and $R^{27}$ independently are hydrogen, unsubstituted lower alkyl, or unsubstituted aryl; or $R^{26}$ and $R^{27}$ are combined with a nitrogen atom to form a heterocyclic group;
—CH($R^{34}$)W, wherein $R^{34}$ is hydrogen or lower alkyl, and W is —N=CHN(alkyl)$_2$; guanidino; $N_3$; $NR^{28}R^{29}$, wherein $R^{28}$ or $R^{29}$ is hydrogen or lower alkyl, and the other is hydrogen, allyl, alkanoyl, aryloxycarbonyl, unsubstituted alkyl, or the residue of an α-amino acid in which the hydroxy group of the carboxyl group is excluded; —CO$_2R^9$; —C(=O) $NR^{10}R^{11}$; —S(=O)$_rR^{30}$, wherein $R^{30}$ is substituted or unsubstituted lower alkyl, aryl, or heteroaryl; or —$OR^{31}$, wherein $R^{31}$ is hydrogen, substituted or unsubstituted alkyl, or substituted or unsubstituted alkanoyl;
—CH=N—$R^{32}$, wherein $R^{32}$ is hydroxyl, lower alkoxy, amino, guanidino, ureido, imidazolylamino, carbamoylamino, or $NR^{26A}R^{27A}$ (wherein $R^{26A}$ is the same as $R^{26}$ and $R^{27A}$ is the same as $R^{27}$); or
—$CH_2Q$ wherein Q is a sugar residue represented by

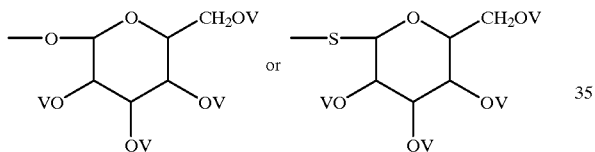

wherein V represents hydrogen, methyl, ethyl, benzyl, acetyl, or trifluoroacetyl;

Y is hydrogen; —OH; —OC(=O)$R^{33}$, wherein $R^{33}$ is alkyl, aryl, or amino; —OCH$_2$O-alkyl; -O-alkyl; aralkyloxy; or X and Y are combined as -X-Y- to form, —CH$_2$OCO$_2$— or —CH$_2$N($R^{16B}$)CO$_2$— (wherein $R^{16B}$ is the same as $R^{16}$);

$A^1$ and $A^2$ are hydrogen, or both are combined to represent O; or $B^1$ and $B^2$ are hydrogen, or both are combined to represent O; or a pharmaceutically acceptable salt thereof; with the proviso that at least one of $A^1,A^2$ or $B^1,B^2$ represents O; and with the further proviso that both X and Y are not simultaneously hydrogen.

Preferably, X is —C(=O)$NR^{26}R^{27}$, carboxyl, lower alkoxycarbonyl, formyl, lower alkyl, —CH$_2OR^{31}$, —CH$_2NR^{28}R^{29}$, or —CH$_2$S (O)$_rR^{30}$. Preferably, $R^1$ and $R^2$ are H. Preferably, $R^3$ is hydrogen or a protecting group. Particularly preferred are Compounds VI, VII, VIII, X, XII, XIV, XV, XVI, XVII, XVIII, XIX, XXV, and XXVII, shown below:

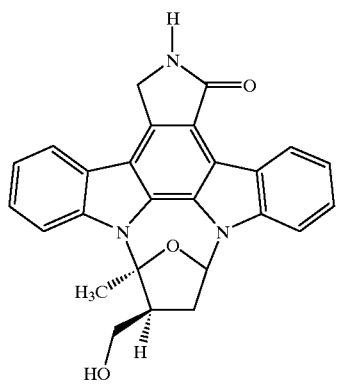

VI

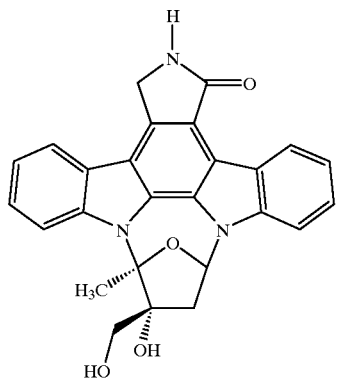

VII

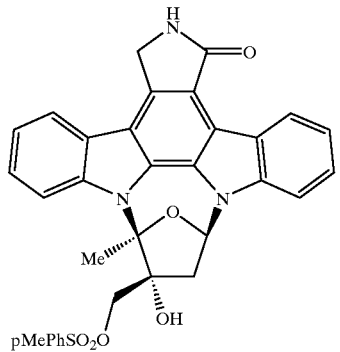

VIII

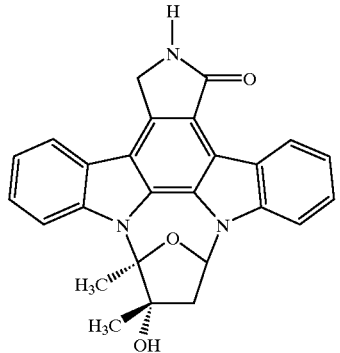

X

XII

XIV

XV

XVI

XVII

XVIII

XIX

W = CH₂, O, S, NH, or R⁴²W = H
R⁴¹ = H or lower alkyl
R⁴² = lower alkyl

XXV

XXVII

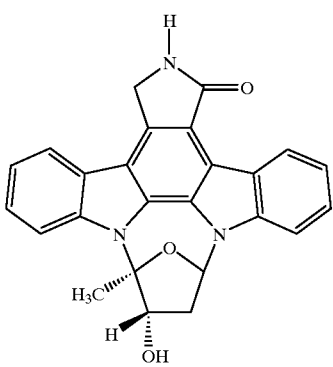

In some embodiments of the invention, 3'-epimeric K252a derivatives are formulated into pharmaceutical compositions.

The invention also provides a method for inhibiting the activity of a tyrosine kinase, for example, protein kinase C (PKC). The method includes contacting the tyrosine kinase with a compound of claim 1. The tyrosine kinase can be in vivo or in vitro.

The invention also provides a method for inhibiting the phosphorylation of a tyrosine kinase by a second kinase. The method includes contacting the second kinase with a compound of claim 1. The tyrosine kinase can be in vivo or in vitro.

The invention also provides a method for enhancing the function of a cholinergic neuron. The method includes contacting the cholinergic neuron with a compound of claim 1. The cholinergic neuron can be in vivo or in vitro.

The invention also provides a method for enhancing the survival of a cholinergic neuron. The method includes contacting the cholinergic neuron with a compound of claim 1. The cholinergic neuron can be in vivo or in vitro.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

Figure 1:
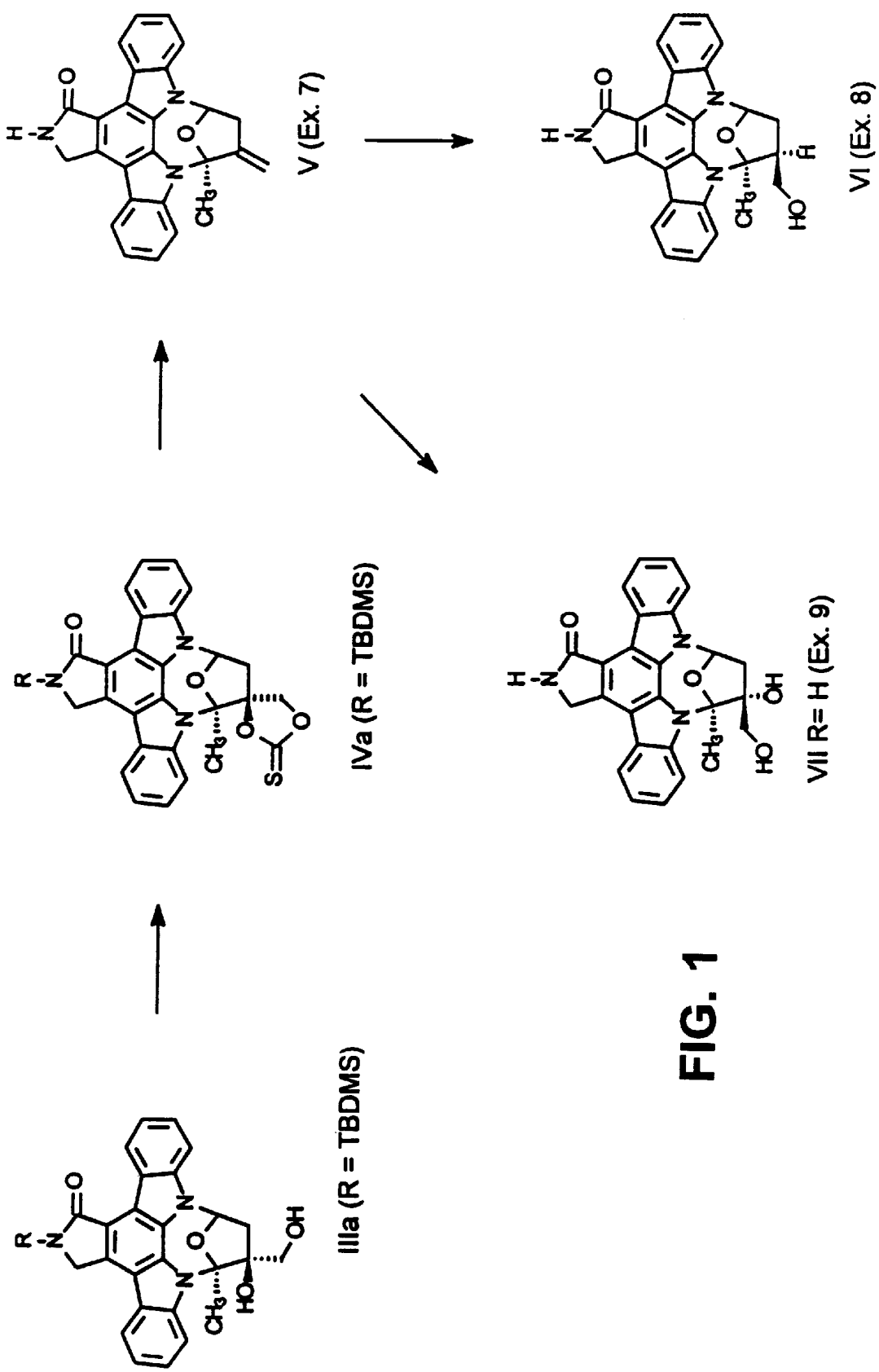
FIG. 1 is a schematic drawing of the synthesis of 3'-epimeric indolocarbazoles VI and VII from the known indolocarbazole IIIa.
Figure 2:
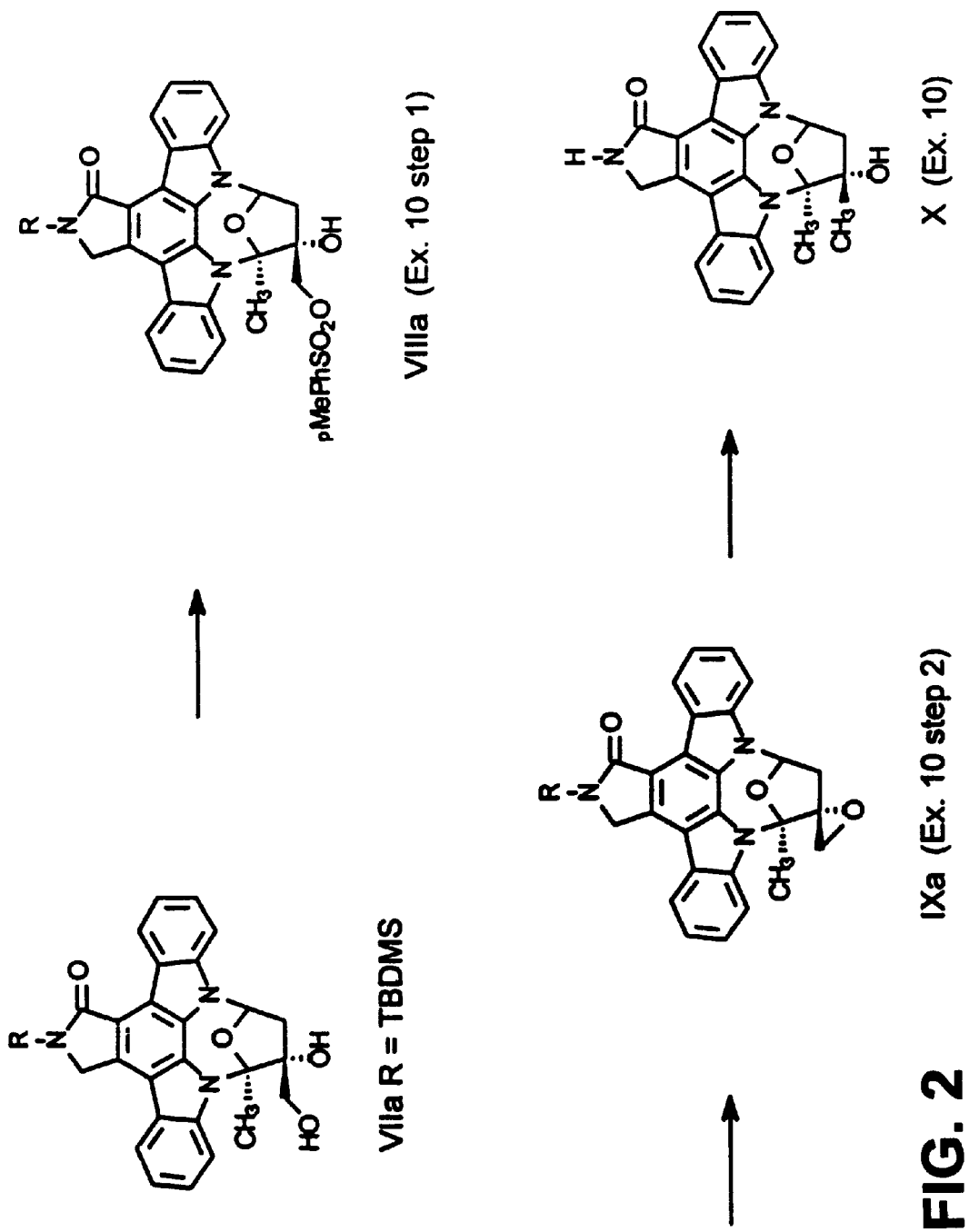
FIG. 2 is a drawing showing the synthesis of the 3'-epimeric indolocarbazole X from the 3'-epimeric indolocarbazole VII, prepared as shown in FIG. 1.

Epimeric K-252a derivatives of the invention display pharmacological activities, including inhibition of tyrosine kinase activity, e.g., inhibition of PKC or trk tyrosine kinase, which inhibition may be useful in treatment of diseases, including cancer. Compounds of the invention are useful for enhancing the function and/or survival of trophic factor responsive cells, e.g., cholinergic neurons. Effects on neurons can be demonstrated in assays including the following: (1) cultured spinal cord choline acetyltransferase ("ChAT") assay; and (2) cultured basal forebrain neuron ("BFN") ChAT activity assay.

ChAT is an enzyme in the biosynthetic pathway leading to acetylcholine. ChAT activity associated with a cholinergic neuron indicates that the neuron is functional. Neuron survival can be assayed by measuring uptake and enzymatic conversion of a dye, e.g., calcein AM, by neurons.

Various neurological disorders are characterized by neuronal cells that are injured, functionally comprised, undergoing axonal degeneration, dying, or at risk of dying. These disorders include: Alzheimer's disease, motor neuron disorders such as amyotrophic lateral sclerosis, Parkinson's disease; cerebrovascular disorders such as stroke or ischaemia, Huntington's disease, AIDS dementia, epilepsy, multiple sclerosis, peripheral neuropathies, disorders induced by excitatory amino acids, and disorders associated with concussive or penetrating injuries of the brain or spinal cord.

Because they enhance trophic factor-induced activities of trophic factor responsive cells, compounds of the invention can be used as therapeutic agents to enhance the function and/or survival of cells of neuronal lineage in a mammal, e.g., a human. In particular, they are useful in treatment of disorders associated with decreased ChAT activity or injury to spinal cord motoneurons.

Chemical Syntheses

Compounds of the invention can be prepared as described below (FIGS. 1–7). The compounds can be prepared by starting with a suitably protected K-252a derivative. K-252a can be protected on the lactam amide nitrogen, e.g., as an acetate or as a silyl derivative.

Thionocarbonate IVa (FIG. 1) can be prepared from diol IIIa using a procedure such as that described in U.S. Pat. No. 4,923,986. Treatment of IVa with trimethylphosphite gives the exocyclic alkene V. Alkene V can be converted to (S)-methanol derivative VI using hydroboration conditions, or converted to (R)-diol VII using osmonium tetraoxide in tetrahydrofuran (THF). In Compound VII, the configuration at the sugar 3'-position is opposite to that reported as (S)-diol III in U.S. Pat. No. 4,923,986.

The (R)-epoxide IXa (FIG. 2) can be prepared by converting (R)-diol VII to the tosyl intermediate VIII, followed by treatment with a base such as sodium hydride or sodium hydroxide. Treatment of (R)-epoxide IXa with hydride reducing agents such as lithium triethyl borohydride gives the tertiary (S)-alcohol X after deprotection of the t-butyldimethyl silyl (TBDMS) group. Chiral alcohol derivatives such as compounds VI, VII or X can be further converted to ether derivatives by reaction with a base and a halide or tosyl partner using conventional techniques. The alcohol derivatives also can be converted to ester derivatives by treatment with acid chlorides or anhydrides, or carbamates by reaction with an appropriate isocyanate by known procedures. Halide or sulfonate derivative of, for example, compounds VI or VII, can be displaced with various O, S, N, or C nucleophiles to yield a suitable derivative.

The preparation of 3'-(R)-K-252a XIV (FIG. 3) begins with ketone XI. Compound XIV differs from the natural K-252a isomer only at the 3' sugar position. Treatment of ketone XIa with cyanide salts (NaCN, KCN, tetrabutylammonium cyanide, or TMSCN) gives a mixture of cyanohydrins XII and XIII. The mixture of cyanohydrin isomers can be separated by chromatography or directly converted to ester XIV or amide XV using HCl in methanol. 3'-epi-K-252a XIV can be hydrolysed to the hydroxy acid XVI using a procedure such as that used for natural K-252a. See, e.g., J. Antibiot.39:1072, 1986. Acid XVI can be converted to a variety of ester or amide derivatives using similar procedures to those described for K-252a. See, e.g., U.S. Pat. Nos. 4,923,986; 5,461,146; and 5,654,427. Amide XV can be reduced to the corresponding methylamine derivative XVII using the procedure described for conversion of natural K-252a, and XVII can be used to prepare a number of methylamide and -urea derivatives. See, e.g., U.S. Pat. Nos. 4,923,986; 5,461,146; and 5,654,427. 3'-epi-K-252a can be reduced to the aldehyde XVIII and condensed with various amines, hydrazines, or hydroxyl amines to form the corresponding analogs. The aldehyde XVIII may be treated with various metal alkyl, arylalkyl, aryl, or heteroarylalkyl reagents, e.g., Li, Mg, Zn or Cu reagents, to form the corresponding alcohol addition products. Aldehyde XVIII may be converted to functionalized olefins and their reduced products by treatment with phosphonium ylides (Quart Rev. 17:406, 1963; Angew Tnt. 16:423, 1977), phosphonates (Horner-Wadsworth-Emmons reagents: Chem. Ber. 91:61, 1958; J. Am. Chem. Soc. 83:1733, 1961; Org. React. 25:73, 1977), silanes (J. Org. Chem. 33:780, 1968; Synthesis 384, 1984) tellurium reagents (Tetrahedron Lett. 28:801, 1987) or boron reagents (Tetrahedron Lett. 24:635, 1983), followed by reduction of the alkene, e.g. by catalytic hydrogenaton. The alkene derived from aldehyde XVIII can be converted to an epoxide and treated, for example, with a nucleophile, as described for epoxide IX.

Epoxide IX (FIG. 4) can be treated with a variety of nucleophiles to form tertiary alcohols of structure XIX. The nucleophile can be substituted. An alternative method (FIG. 5) to prepare epoxides and tertiary 3'-epi-OH configurations of the alcohols is to convert ketone XI to an olefin of structure XX using a conventional olefination reaction, e.g., as described for aldehyde XVIII.

The epoxide of structure XXI can be prepared asymmetrically using known methods. See, e.g., J. Org. Chem. 32:1363, Synthesis 89, 1986; 1967; J. Org. Chem. 60:3692, 1995; J. Am. Chem. Soc. 112:2801, 1990; J. Am. Chem. Soc. 116:6937, 1994; J. Org. Chem. 58:7615, 1993). Nucleophilic epoxide opening in a manner similar to that used with epoxide IX gives the substituted tertiary alcohol with the OH group in the 3'-epi configuration.

The known (R)-alcohol XXVI (FIG. 6) can be converted to (S)-alcohol XXVII using conventional methods for inversion of a secondary alcohol. See, e.g., Tetrahedron Lett. 34:6145, 1996; Synthesis Letters, 1995, 336). Alternatively, XXVII can be prepared by treatment of epoxide XXIV with a hydride reagent such as lithium triethyl borohydride. Ketone XI (FIG. 6) can be converted to triflate XXII followed by treatment with tributyltin hydride to give alkene XXIII.

Known methods used to prepare K252a derivatives with substitutents at positions $R_1$ and $R_2$ can be employed to obtain the corresponding $R_1$ and $R_2$ substitutents on 3'-epi-K-252a. See, e.g., U.S. Pat. Nos. 4,923,986; 5,461,146; and 5,654,427. For example, treatment of XIV (FIG. 7) with one equivalent of N-bromosuccinimide (NBS) yields the derivative XXV in which $R_1$ is Br. Two equivalents of NBS would give the derivative in which both $R_1$ and $R_2$ are Br.

Figure 3:
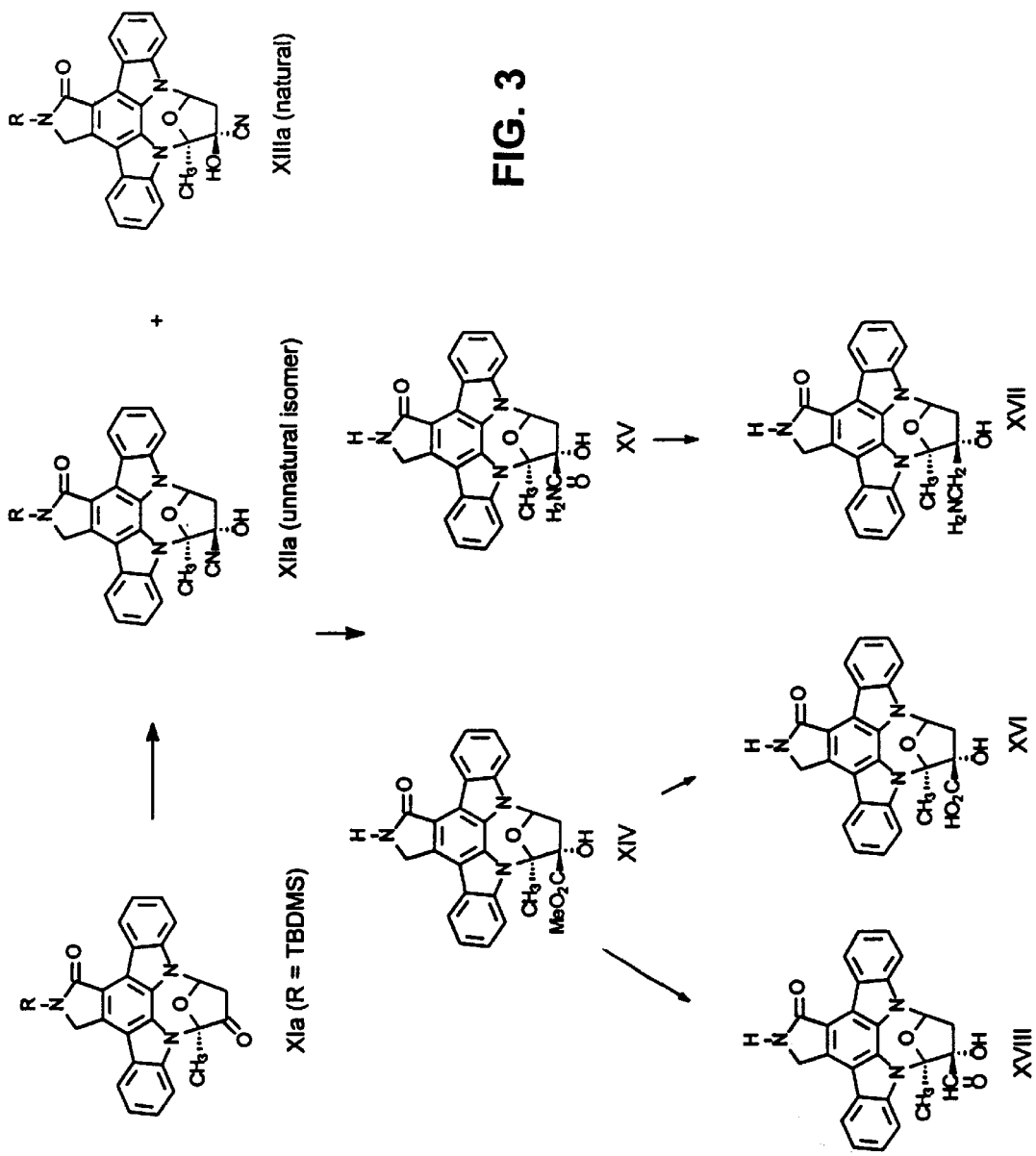
FIG. 3 is a drawing showing the synthesis of 3'-epimeric indolocarbazole XIIa, XIV, XV, XVI, XVII, and XVIII from the intermediate ketone XIa.
Figure 4:
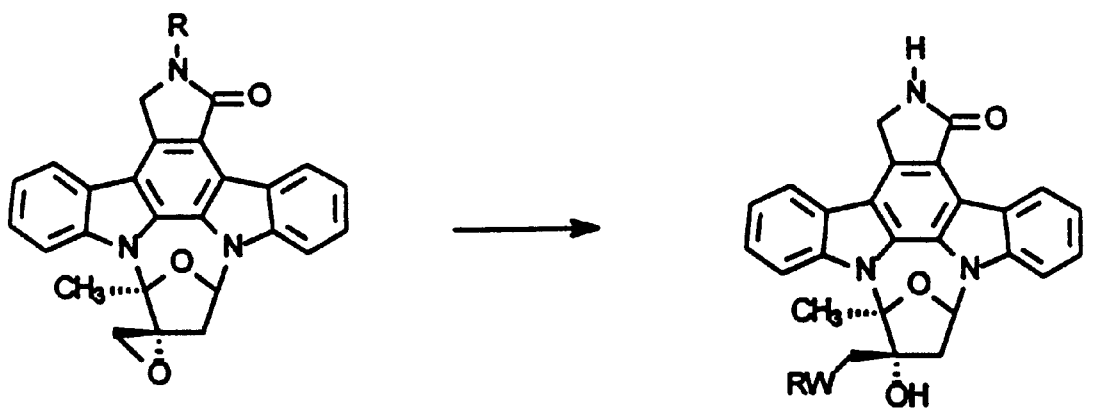
FIG. 4 is a drawing showing the synthesis of 3'-epimeric indolocarbazoles XIX from the intermediate epoxide IXa.
Figure 5:
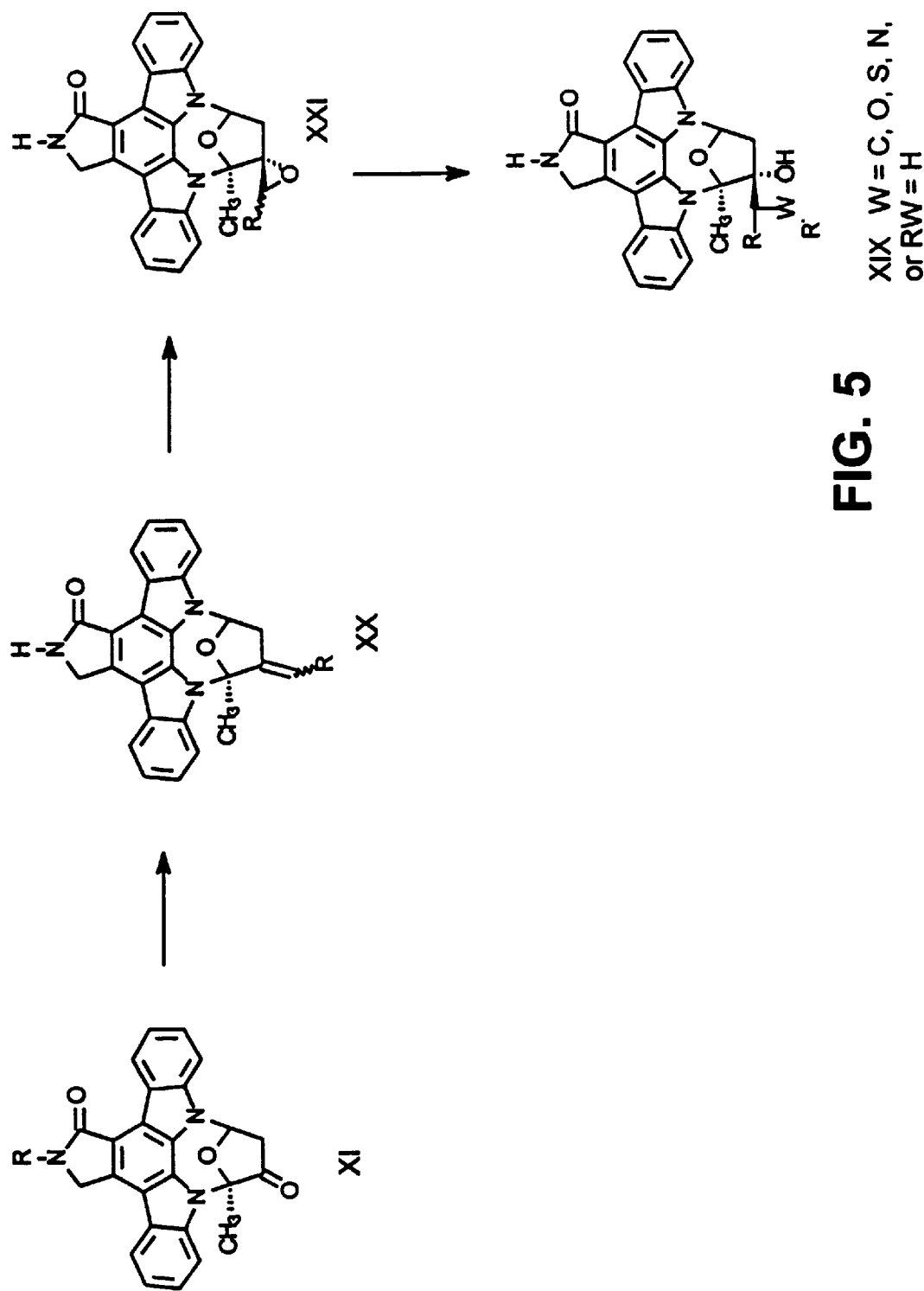
FIG. 5 is a drawing showing an alternate synthesis of the 3'-epimeric indolocarbazoles XIX from the intermediate ketone XI.

Oxidation of (S)-methanol VI to an aldehyde or a carboxylic acid derivative can be achieved using appropriate oxidizing reagents (as described in Oxidations in Organic Chemistry, American Chemical Society Monograph 186, ACS Washington D.C. 1990). The aldehyde or carboxylic acid derivatives can be further transformed using described procedures to prepare derivatives XVI and XVIII (FIG. 3).

Pharmaceutical Compositions

A compound of the invention can be administered to a mammal, e.g., a human patient, as the sole active ingredient or in combination with other therapeutic agents. Compounds of the invention can be formulated into pharmaceutical compositions by admixture with pharmaceutically acceptable excipients and carriers. Such compositions can be formulated for any route of administration, e.g., parenteral, oral, nasal, or topical. The composition can be administered in unit dosage form, following preparation by conventional methods. See, e.g., Remington's Pharmaceutical Sciences (Mack Pub. Co., Easton, Pa.). The amount and concentration of the active ingredient can vary. The concentration will depend upon factors such as the total dosage of the active ingredient, the chemical characteristics (e.g., hydrophobicity) of the compounds employed, the route of administration, the patient's age, the patient's weight, and the condition being treated.

Compounds of the invention can be provided in an physiological buffer solution containing, e.g., 0.1 to 10% w/v compound for parenteral administration. Typical dose ranges are from about 1 μg/kg to about 1 g/kg of body weight per day; a preferred dose range is from about 0.01 mg/kg to 100 mg/kg of body weight per day, and preferably about 0.1 to 20 mg/kg once to four times per day.

The invention includes pharmaceutically acceptable salts of 3'-epimeric K252a derivatives. Pharmaceutically acceptable salts include pharmaceutically acceptable acid addition salts, metal salts, ammonium salts, organic amine addition salts, and amino acid addition salts. Acid addition salts include inorganic acid addition salts such as hydrochloride, sulfate and phosphate, and organic acid addition salts such as acetate, maleate, fumarate, tartrate, citrate and lactate. Examples of metal salts are alkali metal salts such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine.

As used herein, "lower alkyl" means an alkyl group with 1 to 6 carbons. As used herein, "aryl" (alone or in terms such as arylcarbonyl and arylaminocarbonyl) means a group having 6 to 12 carbon atoms, in a single ring, or two fused rings. Examples of aryl groups are phenyl, biphenyl and naphthyl. A heteroaryl group contains at least one hetero atom. Preferably, the hetero atom is O, S, or N. Examples of heteroaryl groups are pyridyl, pyrimidyl, pyrrolyl, furyl, thienyl, imidazolyl, triazolyl, tetrazolyl, quinolyl, isoquinolyl, benzoimidazolyl, thiazolyl and benzothiazolyl. A substituted alkyl group has 1 to 3 independently-selected substituents. Preferred substituents for alkyl groups are hydroxy, lower alkoxy, substituted or unsubstituted arylalkoxy-lower alkoxy, substituted or unsubstituted heteroarylalkoxy-lower alkoxy, halogen, carboxyl, lower alkoxycarbonyl, nitro, amino, mono- or di-lower alkylamino, dioxolane, dioxane, dithiolane, and dithione. A substituted aryl, heteroaryl or arylalkyl group has 1 to 3 independently-selected substituents. Preferred substituents are lower alkyl, hydroxy, lower alkoxy, carboxy, lower alkoxycarbonyl, nitro, amino, mono- or di-lower alkylamino, and halogen.

As used herein, "cholinergic neuron" means a neuron that uses acetylcholine as a neurotransmitter. Examples of cholinergic neurons are basal forebrain neurons, striatal neurons, and spinal cord neurons. As used herein, "sensory neuron" means a neuron responsive to an environmental stimulus such as temperature or movement. Sensory neurons are found in structures including skin, muscle and joints. A dorsal root ganglion neuron is an example of a sensory neuron. As used herein, "trophic factor-responsive cell" means a cell to which a trophic factor binds. Trophic factor-responsive cells include cholinergic neurons, sensory neurons, monocytes and neoplastic cells.

The invention is further illustrated by the following examples. The examples are not to be construed as limiting the scope or content of the invention in any way.

EXPERIMENTAL EXAMPLES

Inhibition of Tyrosine Kinase Activity

Epimeric K252a derivatives were tested for inhibition of kinase activity of baculovirus-expressed human trkA cytoplasmic domain using an ELISA-based assay as described by Angeles et al. (Anal. Biochem. 236:49–55, 1996). A 96-well microtiter plate was coated with substrate solution (recombinant human phospholipase C-γ/glutathione S-transferase fusion protein; Rotin et al., EMBO J., 11:559–567, 1992). Inhibition was measured in 100 ml assay mixtures containing 50 mM Hepes, pH 7.4, 40 μM ATP, 10 mM $MnCl_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat anti-mouse IgG (Bio-Rad). The activity of the bound enzyme was measured using an amplified detection system (Gibco-BRL). Inhibition data were analyzed using the sigmoidal dose-response (variable slope) equation in GraphPad Prism. The concentration that gave 50% inhibition of kinase activity was referred to as $IC_{50}$. Results are summarized in Table 1.

TABLE 1

Inhibition of trkA Kinase Activity by 3'-Epimeric K-252a Derivatives

| Compound | trk $IC_{50}$ (nM) |
|---|---|
| VI | 2 |
| VII | 2 |
| X | 2 |
| XIV | 1.4 |
| XV | 21 |
| XXIX (Control) | 7 |

Inhibition of NGF-stimulated trk Phosphorylation

The inhibition of NGF-stimulated phosphorylation of trk by selected epimeric K-252a derivatives was measured using a procedure modified from that described in U.S. Pat. No. 5,516,771. NIH3T3 cells transfected with trkA were grown in 100 mm dishes. Subconfluent cells were serum-starved by replacing media with serum-free 0.05% BSA-DMEM containing compound (1–100 nM) or DMSO (added to controls) for one hour at 37° C. NGF (Harlan/Bioproducts for Science) was then added to the cells at a concentration of 10 ng/ml for 5 minutes. Cells were lysed in buffer containing detergent and protease inhibitors. Clarified cell lysates were normalized to protein using BCA method and immunoprecipitated with anti-trk antibody.

Polyclonal anti-trk antibody was prepared against a peptide corresponding to the 14 amino acids at the carboxy terminus of trk (Martin-Zanca et al., Mol. Cell. Biol 9:24–33, 1989). The immune complexes were collected on Protein A Sepharose beads (Sigma), separated by SDS polyacrylamide gel electrophoresis (SDS-PAGE), and transferred to a polyvinylidene difluoride (PVDF) membrane. The membrane was immunoblotted with anti-phosphotyrosine antibody (UBI), followed by incubation with horseradish peroxidase coupled goat anti-mouse IgG (Bio-Rad). Phosphorylated proteins were visualized using ECL (Amersham).

The area of the trk protein band was measured and compared to NGF-stimulated control. The inhibition scoring system used, based on percent decrease in trk protein band, was as follows: 0=no decrease; 1=1–25%; 2=26–49%; 3=50–75%; 4=76–100%.

The trk inhibition data (Table 2) revealed that the 3'-epi-OH isomers were more potent for inhibiting trk in a whole cell preparation than the corresponding natural isomers. 3'-epi-K-252a (XIV) displayed an $IC_{50}$ of <10 nM, whereas K-252a displayed an $IC_{50}$ of approximately 50 nM. Compound X showed a complete inhibition of trkA at <50 nM, and an $IC_{50}$ of <10 nM in cells. The natural isomer XXIX did not show complete inhibition at 100 nM. Diol VII displayed greater potency than the natural isomer III for trkA inhibition in NIH3T3 cells.

TABLE 2

Effects of 3'-Epimeric K-252 Derivatives on
NGF-stimulated trkA Phosphorylation in NIH3T3 Cells

| Compound | Inhibition Score | | | |
|---|---|---|---|---|
| | 1 nM | 10 nM | 50 nM | 100 nM |
| K-252a (Control) | 1 | 2 | 3 | 3 |
| XIV | 2 | 4 | 4 | 4 |
| VII | 1 | 2 | 4 | 4 |
| III (Control) | 1 | 2 | 3 | 4 |
| X | 2 | 3 | 4 | 4 |
| XXIX (Control) | 2 | 3 | 3 | 3 |

Inhibition of VEGF Receptor Kinase Activity

3'-Epimeric K-252a derivatives were tested for inhibition of the kinase activity of baculovirus-expressed VEGF receptor kinase domain, using the procedure described above. The kinase reaction mixture, consisting of 50 mM Hepes, pH 7.4, 40 μM ATP, 10 mM $MnCl_2$, 0.1% BSA, 2% DMSO, and various concentrations of inhibitor, was transferred to PLC-γ/GST-coated plates. VEGFR kinase was added and the reaction was allowed to proceed for 15 min. at 37° C. Phosphorylated product was detected by anti-phosphotyrosine antibody (UBI). A secondary enzyme-conjugated antibody was used to capture the antibody-phosphorylated PLC-γ/GST complex. The activity of the bound enzyme was measured by an amplified detection system (Gibco-BRL). Inhibition data were analyzed using the sigmoidal dose-response (variable slope) equation in GraphPad Prism. Results are summarized in Table 3.

TABLE 3

Inhibition of VEGF Receptor Kinase Activity
by 3'-Epimeric K-252a Derivatives

| Compound | VEGFR kinase $IC_{50}$ (nM) |
|---|---|
| VI | 7 |
| VII | 8 |
| X | 17 |
| XIV | 19 |
| XXIX (Control) | 146 |

Inhibition of Protein Kinase C Activity

Protein kinase C activity was measured using the Millipore Multiscreen TCA in-plate assay (Pitt et al., *J. Biomol. Screening*, 1:47–51, 1996). Assays were performed in 96-well Multiscreen-DP plates (Millipore). Each 40-ml assay mixture contained 20 mM Hepes, pH 7.4, 10 mM $MgCl_2$, 2.5 mM EGTA, 2.5 mM $CaCl_2$, 80 mg/ml phosphatidyl serine, 3.2 mg/ml diolein, 200 mg/ml histone H-1 (Fluka), 5 mM [γ-$^{32}$P]ATP, 1.5 ng protein kinase C (UBI; mixed isozymes of a, b, g), 0.1% BSA, 2% DMSO, and 3'-epimeric K-252a derivative. The reaction was allowed to proceed for 10 min at 37° C. The reaction was quenched with ice cold 50% trichloroacetic acid (TCA). The plates were equilibrated for 30 min at 4° C., then washed with ice cold 25% TCA. Scintillation cocktail was added to the plates, and the radioactivity was determined using Wallac MicroBeta 1450 PLUS scintillation counter. The $IC_{50}$ values were calculated by fitting the data to the sigmoidal dose-response (variable slope) equation in GraphPad Prism. The results are summarized in Table 4.

TABLE 4

Inhibitory Effects of 3'-Epimeric K-252a Derivatives
on Protein Kinase C Activity

| Compound | PKC $IC_{50}$ (nM) |
|---|---|
| VI | 95 |
| VII | 79 |
| X | >1000 |
| XIV | 114 |
| XXIX (Control) | 310 |

Enhancement of Spinal Cord ChAT Activity

ChAT was employed a biochemical marker for functional cholinergic neurons. ChAT activity has been used to study the effects of neurotrophins (e.g., NGF or NT-3) on the survival and/or function of cholinergic neurons. The ChAT assay also has been used as an indication of the regulation of ChAT levels within cholinergic neurons.

3'-Epimeric K-252a derivatives increased ChAT activity in the dissociated rat embryonic spinal cord culture assay (Table 5). Compound XVII increased ChAT activity 195% over control cultures (not treated with the epimeric K-252a derivative) after allowing a 2–3 hour plating period for cells to attach to control tissue culture wells. In these assays, a compound was directly added to a dissociated spinal cord culture. Compounds which increased ChAT activity at least 120% of the control activity were considered active. Increased ChAT activity was observed after a single application of a selected epimeric K-252a derivative. Results are summarized in Table 5.

TABLE 5

Enhancement of Spinal Cord ChAT Activity
by 3'-Epimeric K-252a Derivatives
Spinal Cord ChAT
% control

| Compound | Activity at 50 nM | Maximal Activity |
|---|---|---|
| VI | <120 | 125 |
| VII | <120 | 122 |
| X | <120 | 127 |
| XIV | 147 | 195 |
| XV | — | 129 |

Fetal rat spinal cord cells were dissociated, and experiments were performed, essentially as described by Smith et al., *J. Cell Biology* 101:1608–1621, 1985), and Glicksman et al., *J. Neurochem.* 61:210–221, 1993). Dissociated cells were prepared from spinal cords dissected from rats (embryonic day 14–15) by conventional trypsin dissociation techniques. Cells were plated at $6 \times 10^5$ cells/$cm^2$ on poly-l-ornithine coated plastic tissue culture wells in serum-free N2 medium supplemented with 0.05% bovine serum albumin (BSA) (Bottenstein et al., *Proc. Natl. Acad. Sci. USA* 76:514–517, 1979). Cultures were incubated at 37° C. in a humidified atmosphere of 5% $CO_2$/95% air for 48 hours. ChAT activity was measured after 2 days in vitro using a modification of the Fonnum procedure (Fonnum, *J. Neurochem.* 24:407–409, 1975) according to McManaman et al. (*Developmental Biology* 125:311–320, 1988) and Glicksman et al. (supra).

Survival Assay Using Rat Spinal Cord Motoneurons

Figure 8:
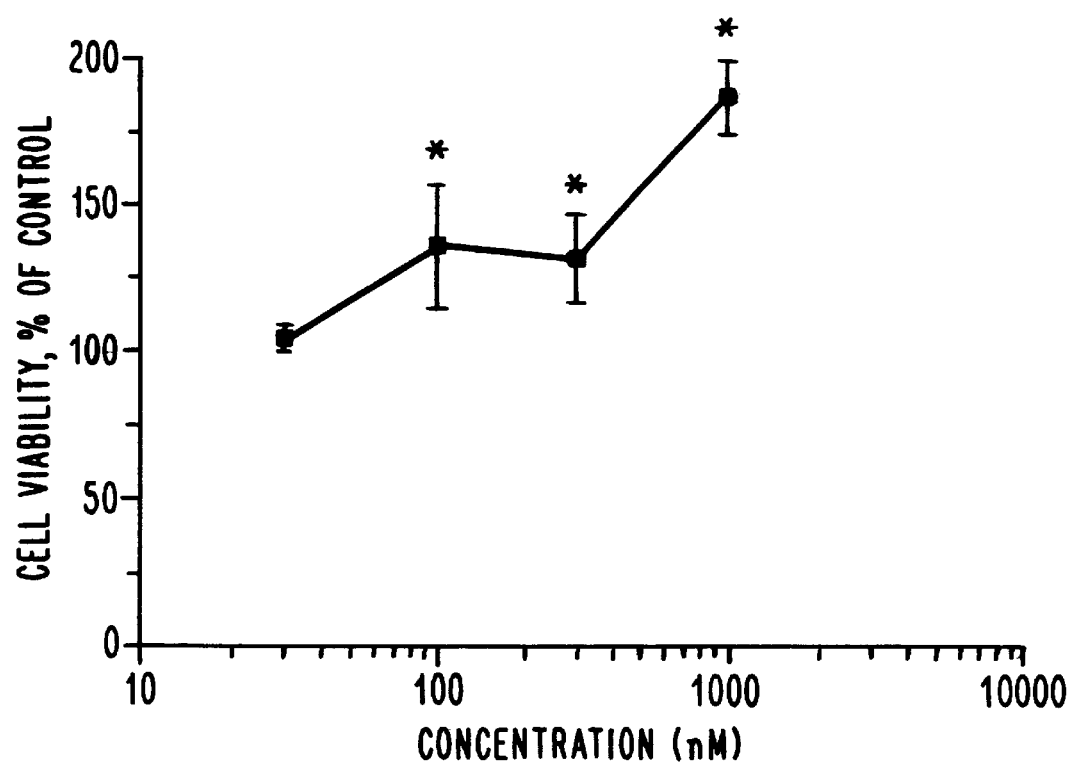
FIG. 8 is a graph summarizing data from experiments to determine the effect of Compound XIV on survival of neurons in cultures enriched for motoneurons. Cell viability (as percent of control) is plotted against concentration of Compound XIV in the cell culture medium.

Selected 3'-epimeric K-252a derivatives were assayed for survival-enhancing activity in rat spinal cord motoneurons. Compound XVI significantly enhanced survival of spinal cord motoneurons (FIG. 8).

Spinal cords were dissected from Sprague-Dawley rat fetuses (Charles River Laboratories, Wilmington, Mass.) of embryonic age (E) 14.5–15. Cells from only the ventral portion of the spinal cord were dissociated, and further enriched for motoneurons by centrifugation on a 6.5% step metrizamide gradient, and were analyzed for purity by staining with low affinity neurotrophin receptor antibody (IgG-192, Boehringer-Mannheim). Cells were seeded onto 96-well plates previously coated with poly-l-ornithine and laminin (5 ug/ml each) at a density of $6 \times 10^4$ cells/cm$^2$ in chemically defined serum-free N2 medium (Bottenstein and Sato, 1979). To distinguish attachment from survival effects, 3,9-bis[(ethylthio)methyl]-K-252a (Kaneko et.al., *J. Med. Chem* 40:1863–1869, 1997) was added to cultures after an initial attachment period of 1–3 hours.

Neuronal survival was assessed after 4 days by calcein AM (Molecular Probes, Eugene, Oreg.) in a fluorimetric viability assay (Bozyczko-Coyne et.al., *J. Neurosci. Meth.* 50:205–216, 1993). Culture medium was serially diluted in Dulbeccos phosphate buffered saline (DPBS). A final concentration of 6 uM calcein AM stock was added to each well. The plates were incubated for 30 min at 37° C., followed by serial dilution washes in DPBS. The fluorescent signal was read using a plate-reading fluorimeter (Cytofluor 2350) (excitation=485 nm; emission=538 nm). For each plate, mean background derived from wells receiving calcein AM, but containing no cells, was subtracted from all values. Linearity of the fluorescence signal was verified for the concentration and incubation time for the range of cell densities. Microscopic counts of neurons correlated directly with relative fluorescence values.

Preparation of Compound V

Compound IVb (U.S. Pat. No. 4,923,986) was dissolved in trimethylphosphite (2 mL) and heated to reflux for 3 hours. The reaction mixture was cooled to room temperature and flushed through a flash silica gel column using chloroform-methanol (20:1) to remove trimethylphosphite. The product was purified by flash chromatography (silica gel; ethyl acetate:hexane; 1:1) to give compound V as a pale yellow solid (15 mg, 95% yield). MS (ESI$^+$): m/e 406 (M+H)$^+$, $^1$H NMR (CDCl$_3$, 300 MHz): δ 2.62 (s, 3H), 2.85 (d, 1H), 3.37–3.45 (m, 1H), 4.95 (s, 1H), 5.00 (s, 2H), 5.09 (s, 1H), 6.29 (s, 1H), 6.90 (d, 1H), 7.33–7.53 (m, 5H), 7.91 (d, 1H), 9.41 (d, 1H).

Preparation of Compound VI

To a stirred solution of compound V (161 mg, 0.397 mmols) in THF (8 mL) at 0° C. under nitrogen was added BH$_3$ THF (1.59 mL of a 1M solution, 1.59 mmol). The reaction mixture was stirred for 30 min at 0° C. and then warmed to room temperature overnight. The mixture was recooled to 0° C. and 10% NaOH (0.1 mL) was added, with vigorous evolution of gas. Hydrogen peroxide (80 mL) was then added dropwise. After stirring at 0° C. for 30 min, the reaction was diluted with ethyl acetate (15 mL) and washed with water (3×10 mL). The organic layer was dried over sodium sulfate, filtered and concentrated in vacuo to a light green solid. The product was purified by chromatography (silica gel: hexane:ethyl acetate; 1:1) to give compound VI as a white solid (0.12 g, 71% yield). MS (ESI$^+$): m/e 424 (M+H)$^+$; $^1$H NMR (CDCl$_3$, 300 MHz): δ 2.54 (s, 3H), 2.51 (m, 1H), 2.99–3.01 (m, 2H), 3.47 (m, 1H), 3.8 (m, 1H), 5.049 (s, 2H), 6.21 (broad 2, 1H), 6.98 (m, 1H), 7.13–7.49 (m, 6H), 7.94–8.02 (m, 2H), 9.34 (d, 1H).

Preparation of Compound VII

To a stirred solution of compound Va (TBDMS-V) (350 mg, 0.673 mmols) in THF (10 mL) at room temperature under nitrogen was added pyridine (0.435 mL, 5.39 mmol) followed by osmium tetroxide (6.73 mL, 0.673 mmol, 0.1 M in CCl$_4$). The reaction mixture was stirred at room temperature 36 h. During this time, the mixture changed color from yellow to orange-brown. Aqueous sodium bisulfite (30 mL) was added to the reaction mixture and the reaction was stirred for 30 min. The reaction mixture was extracted with EtOAc (2×20 mL), dried over sodium sulfate, filtered and concentrated in vacuo to give a light brown film. The mixture was purified by flash chromatography on silica gel using ethyl acetate to yield compound VIIa (TBDMS-VII) as a yellow solid (280 mg, 76% yield). MS (ESI$^+$): m/e 544 (M+H)$^+$, $^1$H NMR (CDCl$_3$, 300 MHz): δ 0.56 (d, 6H), 1.079 (s, 9H), 2.04 (dd, 1H), 2.12 (broad s, 1H), 2.40 (s, 3H), 2.86 (dd, 1H), 3.52 (broad s, 3H), 4.99 (s, 2H), 6.98 (dd, 1H), 7.32 (t, 1H), 7.39–7.46 (m, 4H), 7.97 (dd, 2H), 9.35 (d, 1H).

To a flask containing methanol (2 mL) at 0° C. under nitrogen was added acetyl chloride (4 drops). Compound VIIa (40 mg, 0.072 mmols) in methanol (1 mL) was added dropwise to the solution of methanolic HCl. The reaction mixture was stirred at 0° C. for 1 hour then was warmed to room temperature overnight. The solvent was removed in vacuo to give compound VII as a tan solid (21 mg, 66% yield). MS (ESI$^+$): m/e 440 (M+H)$^+$; $^1$H NMR (CDCl$_3$, 300 MHz): δ 2.052 (dd, 1H), 2.43 (s, 3H), 2.90 (dd, 1H), 3.57 (s, 1H), 3.61 (s, 2H), 5.04 (s, 2H), 6.28 (s, 1H), 7.02 (dd, 1H), 7.33–7.54 (m, 6H), 7.95 (d, 1 H), 8.02 (d, 1H), 9.32 (d, 1H).

Preparation of Compound X

To a stirred solution of intermediate VIIa (FIG. 2; 0.23 g, 0.415 mmols) in THF (10 mL) at 0° C. under nitrogen was added triethylamine (57.9 ml, 0.415 mmols), DMAP (25.4 mg, 0.208 mmol) and p-toluenesulfonyl chloride (79.1 mg, 0.415 mmol). The reaction mixture was stirred at 0° C. for 1 hour. It was then slowly warmed to room temperature overnight. The reaction mixture was warmed for 1 hour, while monitoring by thin layer chromatography (hexane:ethyl acetate, 2:1). The reaction mixture was diluted with ethyl acetate (30 mL) and washed with water (3×15 mL). The organic phase was dried over sodium sulfate, filtered, and concentrated in vacuo to yield the tosyl intermediate VIIIa as a yellow film. The reaction mixture was further purified by flash chromatography on silica gel using hexane:ethyl acetate (2:1) to yield a light yellow film (0.16 g, 55% yield). MS (APCI): m/e 708 (M+H)$^+$; $^1$H NMR (CDCl$_3$, 300 MHz): δ 0.57 (d, 6H), 1.08 (s, 9H), 2.01 (dd, 1H), 2.33 (s, 3H), 2.42 (s, 3H), 3.88 (dd, 1H), 3.86 (dd, 2H), 4.98 (s, 2H), 6.97 (dd, 1H), 7.14 (d, 2H), 7.24–7.49 (m, 7H), 7.75 (d, lH), 7.91 (d, 1H), 9.35 (d, 1H).

To a stirred solution of intermediate VIIIa (0.14 g, 0.198 mmols) in THF (5 mL) at 0° C. under nitrogen was added sodium hydride (15.8 mg, 0.395 mmol). Vigorous evolution of gas was observed, and the reaction mixture became cloudy. Additional sodium hydride (2 eq) was added and the contents of the flask were stirred for an additional 2 hours, then warmed gently for 4 h. The reaction mixture was then cooled to 0° C. and quenched with water. The reaction mixture was diluted with ethyl acetate and washed with water and brine. The organic phase was dried over sodium sulfate, filtered and concentrated in vacuo to give Compound IXa as a yellow film (100.2 mg, 95% yield). MS (APCI): m/e 536 (M+H)$^+$; $^1$H NMR (CDCl$_3$, 300 MHz): δ 0.56 (d, 6H), 1.08 s, 9H), 2.32–2.38 (m, 4H), 2.57 (d, 2H), 3.01 (dd, 1H), 4.99 (s, 2H), 7.01 (d, 1H), 7.33–7.56 (m, 5H), 7.73 (d, 1H), 7.94 (d, 1H), 9.46 (d, 1H).

To a stirred solution of Compound IXa (100 mg, 0.187 mmol) in THF (5 mL) at 0° C. under nitrogen was added lithium triethyl-borohydride (0.37 mL of 1M solution in THF, 0.374 mmol) dropwise, with evolution gas. Additional lithium triethylborohydride (2 eq) was added at 0° C. and the reaction was stirred at 0° C. for 30 minutes and then was warmed to room temperature. The reaction mixture was cooled to 0° C. and quenched with water, diluted with ethyl acetate and washed with water and brine. The organic phase was dried over magnesium sulfate filtered and concentrated in vacuo. The reaction mixture was purified by flash chromatography on silica gel using hexane:ethyl acetate (1:1) to yield Xa (R=TBDMS) as a pale yellow film. To a stirred solution of Compound Xa in methanol at 0° C. under nitrogen was added a solution made from acetyl chloride (5 drops) in methanol. The reaction mixture was stirred at 0° C. for 30 minutes, then was warmed to room temperature overnight. The solvent was removed in vacuo leaving a yellow solid which was purified by silica gel chromatography (hexane:ethyl acetate;1:1) to give Compound X (30 mg, 42%). MS (ESI$^+$): m/e 424 (M+H)$^+$, $^1$H NMR (CDCl$_3$, 300 MHz): δ 1.39 (s, 3H), 2.29 (dd, 1H), 2.37 (s, 3H), 2.91 (dd, 1H), 5.05 (s, 2H), 6.19 (s, 1H), 6.97 (t, 1H), 7.32–7.50 (m, 5H), 7.78 (d, 1H), 7.95 (d,1H), 9.33 (d, 1H).

Preparation of Compounds XIV and XV

To a stirred solution of ketone XI (U.S. Pat. No. 4,923,986) (FIG. 5; 451 mg, 1.11 mmols) in a CH$_2$Cl$_2$-dioxane mixture (6 mL; 5:1) under nitrogen was added tetrabutylammonium cyanide (740 mg, 2.77 mmols) and acetic acid (95 mL, 1.66 mmols) at room temperature. The dark reaction mixture was stirred for 24 hours, and then concentrated in vacuo. The dark oil was dissolved in ethyl acetate (20 mL) and dioxane (2 mL) and washed with water (3×10 mL) and brine (1×10 mL). The organic phase was dried over magnesium sulfate, filtered, and concentrated in vacuo to a brown solid. The HPLC analysis showed the presence of two cyanohydrin intermediates, XIIa and XIIIb.

To a flask containing methanol (4 mL) was added HCl(g) for 10 minutes. A solution of the crude cyanohydrin mixture from step 1 (450 mg, 1.04 mmols) in methanol:dioxane (2:1, 3 mL) was added to the HCl in methanol solution at 0° C. The reaction mixture was sealed and stirred at 0° C. for 2 hours, then was placed in a refrigerator for 48 h. The flask was warmed to room temperature and 6 N HCl was added carefully. The mixture was stirred for 30 minutes and then concentrated to dryness. The residue was dissolved in 50% methanol:water and a precipitate formed while stirring overnight at room temperature. The reaction mixture was concentrated to dryness. The residue was purified by flash chromatography on silica gel using hexane:ethyl acetate (1:1) to yield compound XIV as an off-white solid. MS (ESI$^+$): m/e 468 (M+H)$^+$; $^1$H NMR (CDCl$_3$, 300 MHZ) δ 2.416 (s, 3H, 2.77 (dd, 1H), 2.91 (s, 3H), 2.952 (dd, 1H), 4.99 (s, 2H), 7.13 (dd, 1H), 7.33 (t, 1H), 7.44 (dd, 2H), 7.64 (t, 2H), 7.98 (d, 1H), 9.16 (d, 1H). The column was eluted with ethyl acetate to obtain the amide XV as a light orange product (13 mg). MS (ESI): m/e 453 (M+H)$^+$; $^1$H NMR (DMSO-d$_6$, 300 MHz) δ 2.33 (s, 3H), 2.87 (m, 2H), 4.94 (s, 2H), 6.58 (s, 1H), 7.19–7.64 (m, 6H), 7.81 (m, 3H), 7.96 (d, 1H), 8.59 (s, 1H), 9.17 (d, 1H).

Preparation of Compound XXIII

Figure 6:
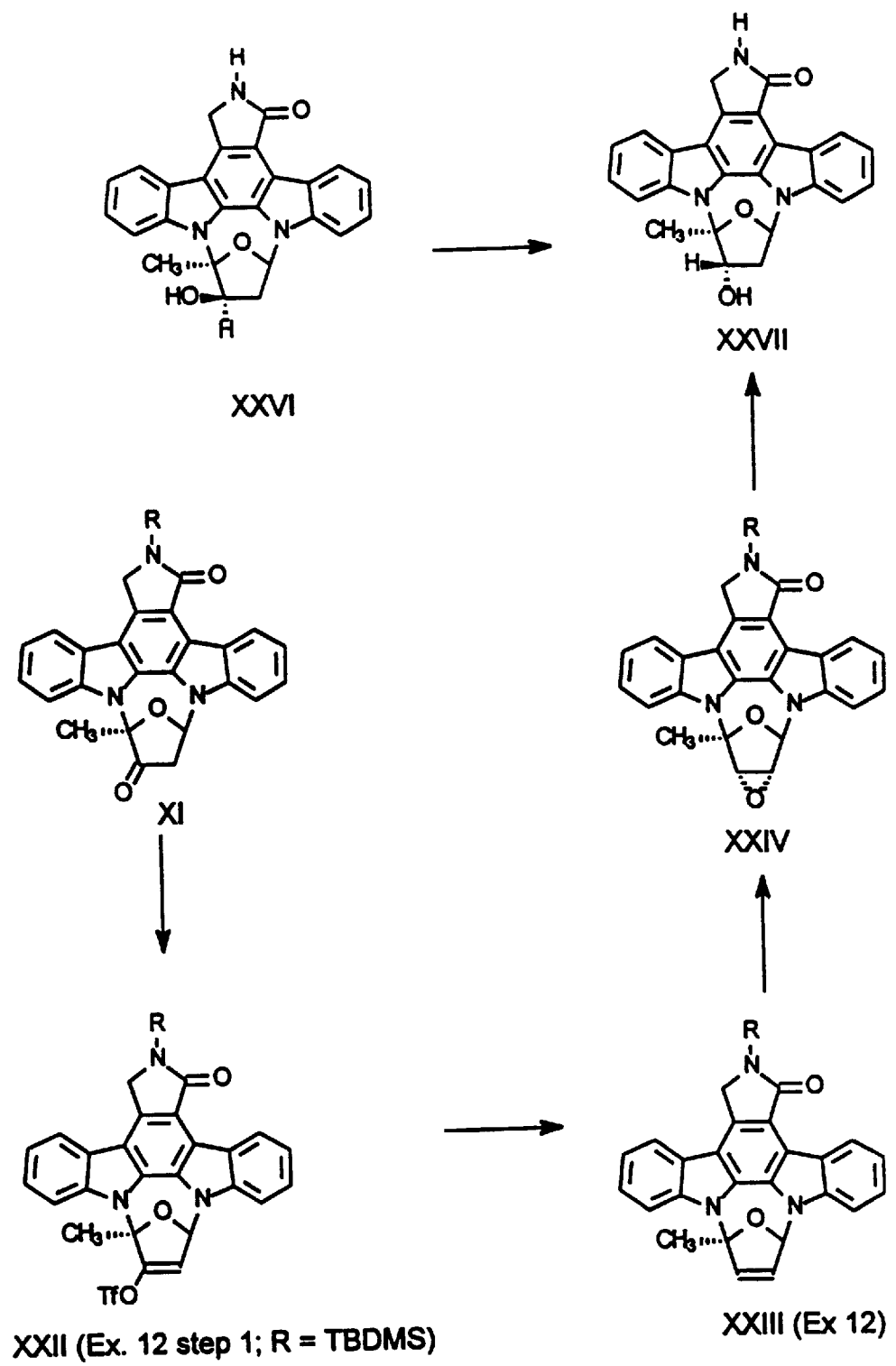
FIG. 6 is a drawing showing the synthesis of the epimeric 3'-hydroxyindolocarbazole XXVII from the intermediate ketone XI, and alternatively by epimerization of the known 3'-hydroxyindolocarbazole XXVI.
Figure 7:
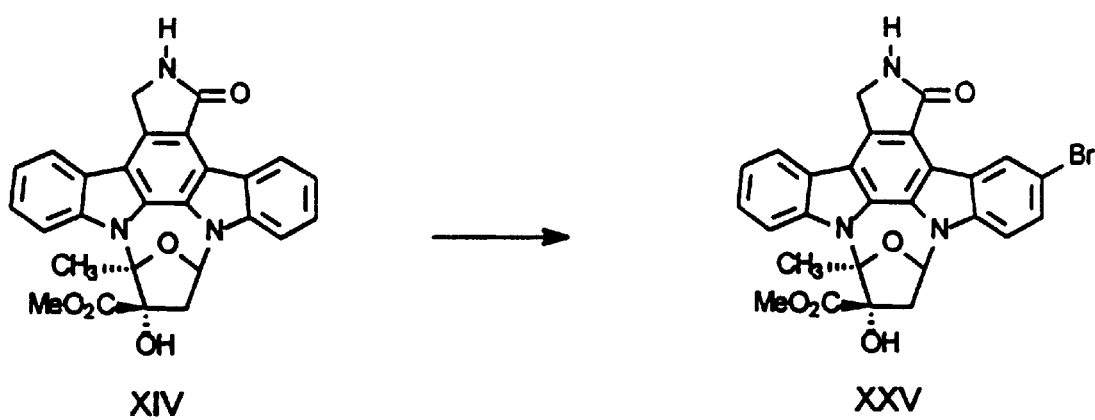
FIG. 7 is a drawing showing the synthesis of a ring-brominated 3'-epimeric indolocarbazole XXV from the corresponding 3'-epimeric indolocarbazole XIV.

To a stirred solution of ketone XIa (FIG. 6; R=TBDMS) (95.4 mg, 0.183 mmol) in THF (5 mL) at −78° C. under nitrogen was added lithium diethylamide (0.12 mL, 1.5M solution in cyclohexane). The reaction mixture stirred at −78° C. for 30 min. A solution of N-phenyltrifluoromethanesulfonimide (71.9 mg, 0.201 mmol) in THF (1.5 mL) was added dropwise to the reaction mixture and the mixture was stirred at −78° C. for 30 min. The reaction mixture was allowed to warmed to 0° C., stirred for 1 hour, then warmed to room temperature overnight. The reaction was quenched with ammonium chloride (sat. aq. 2 mL), diluted with ethyl acetate and washed with water. The mixture was purified by flash chromatography on silica gel using hexane:ethyl acetate (2:1) to give compound XXIIa (R=TBDMS) as an off-white solid (66 mg, 61% yield). MS (ESI$^+$): m/e 654 (M+H)$^+$, $^1$H NMR (CDCl$_3$, 300 MHz): δ 0.58 (s, 6H), 1.12 (s, 9H), 2.66 (s, 3H), 5.02 (dd, 2H), 6.14 (s, 1H), 7.31–7.62 (m, 6H), 7.83 (d, 1H), 7.98 (d, 1H), 9.44 (d, 1H).

To a stirred solution of the product from step 1 (compound XXIIa) (75 mg, 0.115 mmol) in THF (10 mL) was added lithium chloride (14.6 mg, 0.345 mmol) and tetrakis-(triphenylphosphine)palladium (0) (2.6 mg, 0.0023 mmol). Tributyltin hydride (37 mL, 0.139 mmol) was added dropwise and the contents were heated to 60° C. The reaction mixture was heated for 4 h, during which time the color of the reaction changed from yellow to red-black. The reaction was concentrated in vacuo and purified by flash chromatography on silica gel using hexane:ethylacetate (2:1). Two products were isolated: TBDMS-protected XXIIIa product contaminated with tributyltin (60 mg) and deprotected product XXIII (10 mg, 22%). MS (ESI): m/e 392 (M+H)$^+$, $^1$H NMR (CDCl$_3$, 300 MHz): δ 2.65 (s, 3H), 4.978 (s, 2H), 6.19 (d, 1H), 6.28 (d, 1H), 6.41 (s, 1H), 7.26–7.62(m, 5H), 7.65–7.69 (m, 1H), 7.87 (dd, 2H), 9.39 (d, 1H).

Compound XXIII displayed the following IC$_{50}$ values in the assays described above: inhibition of trkA kinase, 4 nM; inhibition of VEGF receptor kinase, 25 nM, and inhibition of Protein Kinase C, >1000 nM.

Preparation of Compound XXV

To a stirred solution of compound XIV (30.4 mg, 0.065 mmols) in THF (5 mL) at room temperature under nitrogen was added N-bromosuccinimide (11.6 mg, 0.065 mmols) in one portion. The reaction mixture was light orange in color initially and gradually turned light purple. The reaction mixture stirred at room temperature overnight. The solvent was removed in vacuo and the solid purified by flash chromatography on silica gel using hexane-ethyl acetate (2:1). This yielded Compound XXV as an off-white solid (31.2 mg, 88% yield). MS (ESI): m/e 547 (M+H)+, 1H NMR (CDCl3, 300 MHz): δ 2.42 (s, 3H), 2.77–2.83 (m, 1H), 2.86 (3H, s), 31.66 (dd, 1H), 4.105 (s, 1H), 5.07 (s, 2H), 6.39 (s, 1H), 7.01 (dd, 1H), 7.95 (d, 1H), 7.58 (d, 1H), 7.34–7.57 (m, 4H), 9.50 (s, 1H).

Preparation of Compound XXIX

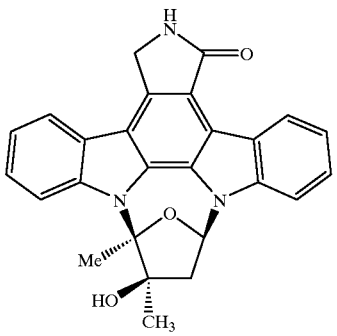

XXIX

Method A

To a stirred solution of epoxide XXVIII (U.S. Pat. No. 4,923,986, compound I-27) (90.1 mg, 0.152 mmol) in THF (4 mL) at 0° C. under nitrogen was added lithium triethylborohydride (0.455 mL of a 1M in THF soln., 0.455 mmols) dropwise. The reaction mixture was stirred at 0° C. for 1 hour then allowed warmed to room temperature overnight. The mixture was cooled to 0° C. and quenched by the slow addition of methanol. Stirring was continued at 0° C. for 15 min, after which time the reaction mixture was warmed to room temperature. The solvent was removed in vacuo. This yielded a yellow oil. The oil was purified by flash chromatography on silica using ethyl acetate:hexane (1:1). This yielded Compound XXIX as a white solid (75 mg, 83% yield). MS (ESI): m/e 424 (M+H)$^+$; $^1$H NMR (CDCl$_3$, 300 MHz): δ 1.69 (s, 3H), 1.99 (s, 3H), 2.86 (dd, 1H), 3.03 (dd, 1H), 4.37 (m, 3H), 4.93 (s, 2H), 6.43 (t, 1H), 6.95 (d, 1H), 7.03 (t, 1H), 7.18 (t, 1H), 7.44 (t, 1H), 7.79 (d, 1H), 7.99 (d, 1H), 8.69 (d, 1H).

Method B

To a stirred solution of ketone XI (FIG. 3, R=H) (212 mg, 0.41 mmols) in THF (6mL) at 0° C. under nitrogen was added methylmagnesium iodide (0.27 mL, 0.82 mmol) dropwise. The reaction mixture stirred at 0° C. for 1 hour then was warmed to room temperature overnight. The mixture was then heated to reflux for 24 h then cooled to room temperature. The reaction was quenched with ammonium chloride (sat. aq.), diluted with ethyl acetate (20 mL) and washed with water (3×10 mL). The organic phase was dried over sodium sulfate, filtered, and concentrated in vacuo to a yellow residue. The product was purified by flash chromatography on silica gel using hexane:ethyl acetate (1:1) to give compound XXIX as a tan solid (0.11 g, 50% yield). The $^1$H NMR and mass spectrometry data were consistent with the product obtained from Method A.

Other embodiments are within the following claims.

We claim:

1. A compound of the formula:

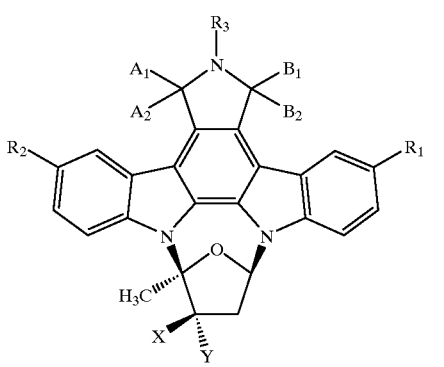

II wherein:

$R^1$ and $R^2$ indepently are:
  hydrogen; lower alkyl; halogen; acyl; nitro; sulfonic acid;
  —CH=NR$^4$, wherein R$^4$ is guanidino, heterocyclic, or —NR$^5$R$^6$, wherein R$^5$ or R$^6$ is hydrogen or lower alkyl, and the other is hydrogen, lower alkyl, acyl, aryl, heterocyclic, carbamoyl or lower alkylaminocarbonyl;
  —NR$^5$R$^6$;
  —CH(SR$^7$)$_2$, wherein R$^7$ is lower alkyl or alkylene;
  —(CH$_2$)$_j$R$^8$, wherein j is 1–6, and R$^8$ is halogen; substituted aryl; unsubstituted aryl; substituted heteroaryl; unsubstituted heteroaryl; N$_3$;
  —CO$_2$R$^9$, wherein R$^9$ is hydrogen, substituted lower alkyl, unsubstituted lower alkyl, substituted aryl, unsubstituted aryl, substituted heteroaryl, or unsubstituted heteroaryl;
  —C(=O)NR$^{10}$R$^{11}$, wherein R$^{10}$ and R$^{11}$ independently are hydrogen, substituted lower alkyl, unsubstituted lower alkyl, substituted aryl, unsubstituted aryl, substituted heteroaryl, unsubstituted heteroaryl, substituted aralkyl, unsubstituted aralkyl, lower alkylaminocarbonyl, or lower alkoxycarbonyl, or R$^{10}$ and R$^{11}$ are combined with a nitrogen atom to form a heterocyclic group;
  —OR$^{12}$, wherein R$^{12}$ is hydrogen, substituted lower alkyl, unsubstituted lower alkyl, substituted aryl, unsubstituted aryl; or —C(=O)R$^{13}$, wherein R$^{13}$ is hydrogen, NR$^{10}$R$^{11}$, substituted lower alkyl, unsubstituted lower alkyl, substituted aryl, unsubstituted aryl, substituted heteroaryl, unsubstituted heteroaryl, substituted aralkyl, or unsubstituted aralkyl;
  —NR$^{10}$R$^{11}$;
  —C(=O)R$^{14}$, wherein R$^{14}$ is hydrogen, lower alkyl, substituted aryl, unsubstituted aryl, substituted heteroaryl, or unsubstituted heteroaryl;
  —S(=O)$_r$R$^{15}$, wherein r is 0 to 2, and R$^{15}$ is hydrogen, substituted lower alkyl, unsubstituted lower alkyl, substituted aryl, unsubstituted aryl, substituted heteroaryl, unsubstituted heteroaryl, substituted aralkyl, unsubstituted aralkyl, thiazolinyl, (CH$_2$)$_a$CO$_2$R$^{16}$, wherein a is 1 or 2, and R$^{16}$ is hydrogen or lower alkyl, or —CH$_2$)$_a$C(=O)NR$^{10}$R$^{11}$;
  —OR$^{17}$, wherein R$^{17}$ is hydrogen, lower alkyl, or —C(=O)R$^{18}$, wherein R$^{18}$ is substituted lower alkyl, unsubstituted lower alkyl, substituted aryl, or unsubstituted aryl;
  —C(=O)(CH$_2$)$_j$R$^{19}$, wherein R$^{19}$ is hydrogen, halogen, NR$^{10}$R$^{11}$, N$_3$, SR$^{15}$, or OR$^{20}$, wherein R$^{20}$ is hydrogen, substituted lower alkyl, unsubstituted lower alkyl, or C(=O)R$^{14}$;
  —CH(OH)(CH$_2$)$_j$R$^{19}$;
  —(CH$_2$)$_d$CHR$^{21}$CO$_2$R$^{16A}$, wherein d is 0–5, and R$^{21}$ is hydrogen, CONR$^{10}$R$^{11}$, or CO$_2$R$^{16A}$, wherein R$^{16A}$ is the same as R$^{16}$;
  —(CH$_2$)$_d$CHR$^{21}$CONR$^{10}$R$^{11}$;
  —CH=CH(CH$_2$)$_m$R$^{22}$, wherein m is 0–4, and R$^{22}$ is hydrogen, lower alkyl, CO$_2$R$^9$, substituted aryl, unsubstituted aryl, substituted heteroaryl, unsubstituted heteroaryl, OR$^{12}$, or NR$^{10}$R$^{11}$;
  —CH=C(CO$_2$R$^{16A}$)$_2$;
  —C≡C(CH$_2$)$_m$R$^{22}$;
  —SO$_2$NR$^{23}$R$^{24}$, wherein R$^{23}$ and R$^{24}$ independently are hydrogen, lower alkyl, or groups that form a heterocycle with the adjacent nitrogen atoms;
  —OCO$_2$R$^{13A}$, wherein R$^{13A}$ is the same as R$^{13}$; or
  —OC(=O)NR$^{10}$R$^{11}$;

R$^3$ is hydrogen; lower alkyl; carbamoyl; amino; tetrahydropyranyl; hydroxyl; C(=O)H; aralkyl; lower alkanoyl; or CH$_2$CH$_2$R$^{25}$, wherein R$^{25}$ is halogen, amino, di-lower alkylamino, hydroxyl, or hydroxysubstituted lower alkylamino;

X is hydrogen; formyl; carboxyl; lower alkoxycarbonyl; lower alkylhydrazinocarbonyl; —CN; lower alkyl;
  —C(=O)NR$^{26}$R$^{27}$, wherein R$^{26}$ and R$^{27}$ independently are hydrogen, unsubstituted lower alkyl, or unsubstituted aryl; or R$^{26}$ and R$^{27}$ are combined with a nitrogen atom to form a heterocyclic group;

—CH(R³⁴)W, wherein R³⁴ is hydrogen or lower alkyl, and W is —N=CHN(alkyl)₂; guanidino; N₃; NR²⁸R²⁹, wherein R²⁸ or R²⁹ is hydrogen or lower alkyl, and the other is hydrogen, allyl, alkanoyl, aryloxycarbonyl, unsubstituted alkyl, or the residue of an α-amino acid in which the hydroxy group of the carboxyl group is excluded; —CO₂R⁹; —C(=O)NR¹⁰R¹¹; —S(=O)ᵣR³⁰, wherein R³⁰ is substituted or unsubstituted lower alkyl, aryl, or heteroaryl; or —OR³¹, wherein R³¹ is hydrogen, substituted or unsubstituted alkyl, or substituted or unsubstituted alkanoyl;

—CH=N—R³², wherein R³² is hydroxyl, lower alkoxy, amino, guanidino, ureido, imidazolylamino, carbamoylamino, or NR²⁶ᴬR²⁷ᴬ (wherein R²⁶ᴬ is the same as R²⁶ and R²⁷ᴬ is the same as R²⁷); or —CH₂Q wherein Q is a sugar residue represented by

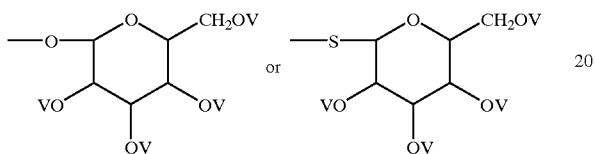

wherein V represents hydrogen, methyl, ethyl, benzyl, acetyl, or trifluoroacetyl;

Y is hydrogen; —OH; —OC(=O)R³³, wherein R³³ is alkyl, aryl, or amino; —OCH₂O-alkyl; -O-alkyl; aralkyloxy; or X and Y are combined as -X-Y- to form, —CH₂OCO₂— or —CH₂N(R¹⁶ᴮ)CO₂— (wherein R¹⁶ᴮ is the same as R¹⁶);

A¹ and A² are hydrogen, or both are combined to represent O; or B¹ and B² are hydrogen, or both are combined to represent O; or a pharmaceutically acceptable salt thereof; with the proviso that at least one of A¹,A² or B¹,B² represents O; and with the further proviso that both X and Y are not simultaneously hydrogen.

2. The compound of claim 1, wherein X is —C(=O)NR²⁶R²⁷, carboxyl, lower alkoxycarbonyl, formyl, lower alkyl, —CH₂OR³¹, —CH₂NR²⁸R²⁹, or —CH₂S(O)ᵣR³⁰.

3. The compound of claim 1, wherein R¹ and R² are H.

4. The compound of claim 1, wherein R³ is hydrogen or a protecting group.

5. The compound of claim 1, wherein the compound is selected from the group consisting of (Compounds VI, VII, VIII, X, XII, XIV, XV, XVI, XVII, XVIII, XIX, XXV, and XXVII):

VI

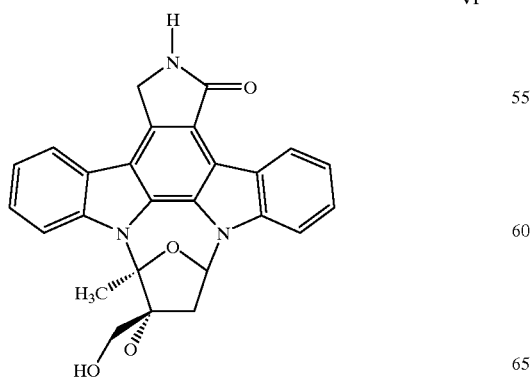

VII

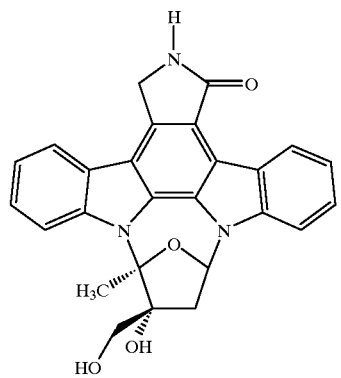

VIII

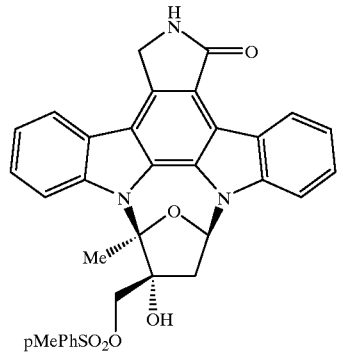

X

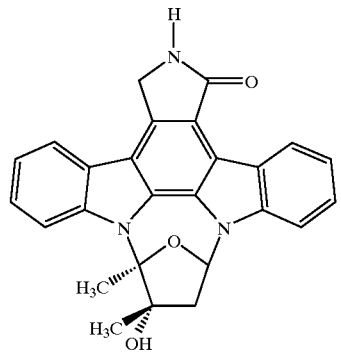

XII

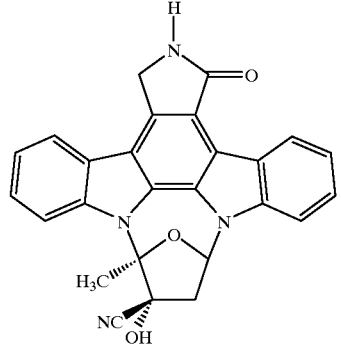

XIV
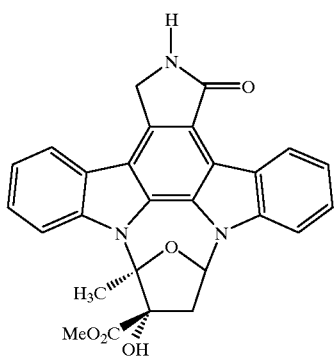
XV
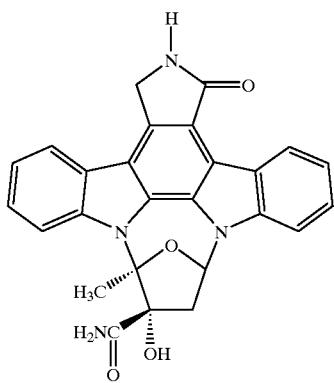
XVI
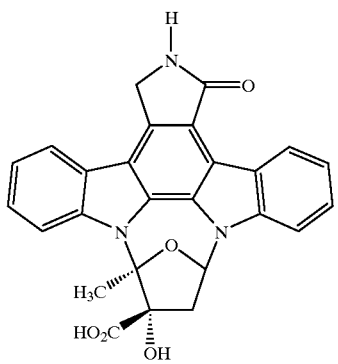
XVII
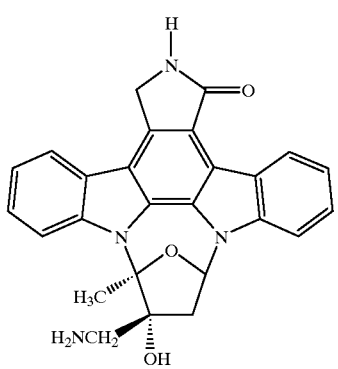
XVIII
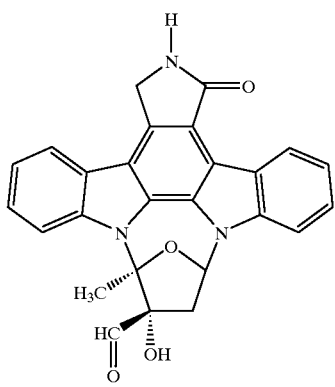
XIX
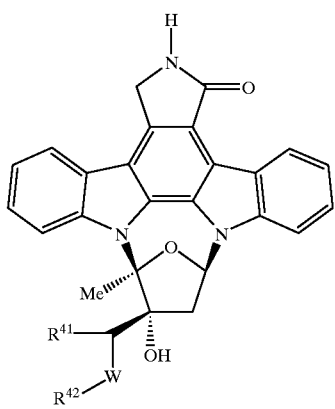
W = CH$_2$, O, S, NH, or R$^{42}$W = H
R$^{41}$ = H or lower alkyl
R$^{42}$ = lower alkyl
XXV
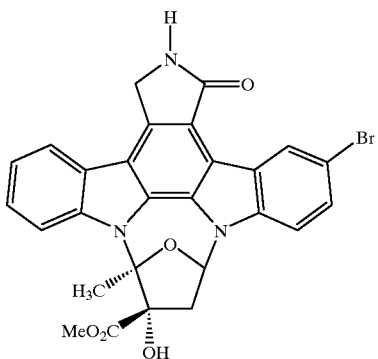
XXVII
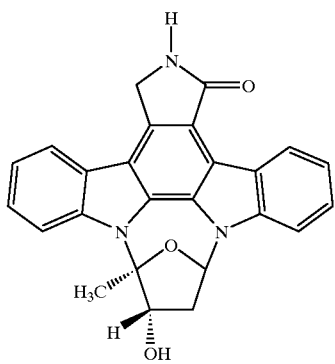

6. A pharmaceutical composition comprising a compound according to claim 1.

7. A method for inhibiting the activity of a tyrosine kinase, comprising contacting the tyrosine kinase with a compound of claim 1.

8. The method of claim 7, wherein the tyrosine kinase is protein kinase C.

9. The method of claim 7, wherein the tyrosine kinase is trkA.

10. A method for inhibiting the phosphorylation of a tyrosine kinase by a second kinase, comprising contacting the second kinase with a compound of claim 1.

11. A method for enhancing the function of a cholinergic neuron, comprising contacting the cholinergic neuron with a compound of claim 1.

12. A method for enhancing the survival of a cholinergic neuron, comprising contacting the cholinergic neuron with a compound of claim 1.

* * * * *

UNITED STATES PATENT AND TRADEMARK OFFICE
CERTIFICATE OF CORRECTION

PATENT NO.    : 6,093,713
DATED         : July 25, 2000
INVENTOR(S)   : Hudkins et al.

It is certified that error appears in the above-identified patent and that said Letters Patent is hereby corrected as shown below:

<u>Column 3,</u>
Lines 3-4, please delete "hydroxysubstituted" and insert -- hydroxy substituted -- therefor.

<u>Column 16,</u>
Line 17, please delete "compound Vila" and insert -- compound VIIa -- therefor.

Signed and Sealed this

Twelfth Day of August, 2003

JAMES E. ROGAN
*Director of the United States Patent and Trademark Office*